United States Patent [19]

Dikstein

[11] Patent Number: 5,106,615

[45] Date of Patent: Apr. 21, 1992

[54] EYEDROPS HAVING NON-NEWTONIAN RHEOLOGICAL PROPERTIES

[76] Inventor: Shabtay Dikstein, 7 Banai Street, Jerusalem, Israel

[21] Appl. No.: 620,102

[22] Filed: Nov. 30, 1990

Related U.S. Application Data

[63] Continuation-in-part of Ser. No. 350,286, May 11, 1989, abandoned, which is a continuation-in-part of Ser. No. 107,575, Oct. 13, 1987, abandoned.

[30] Foreign Application Priority Data

Oct. 14, 1986 [IL] Israel ......................................... 80298

[51] Int. Cl.$^5$ ....................... A61K 31/78; A61K 31/74
[52] U.S. Cl. .................................. 424/78.04; 514/912; 424/78.31; 424/78.32
[58] Field of Search ...................... 424/81, 78; 514/912

[56] References Cited

U.S. PATENT DOCUMENTS

| 4,540,568 | 9/1985 | Tragar et al. | 574/912 |
| 4,620,979 | 11/1986 | Schachar | 574/912 |

FOREIGN PATENT DOCUMENTS

| 8404680 | 12/1984 | PCT Int'l Appl. | 514/912 |
| 8404681 | 12/1984 | PCT Int'l Appl. | 514/912 |

OTHER PUBLICATIONS

Survey of Opthalmology, vol. 22, No. 2, Sep.–1977, pp. 69–87, Holly et al.

*Primary Examiner*—Thurman K. Page
*Assistant Examiner*—Peter F. Kulkosky
*Attorney, Agent, or Firm*—Browdy and Neimark

[57] ABSTRACT

Isotonic humectant eyedrops which have pronounced non-Newtonian rheological properties, simulating the rheological behavior of human tears. The eyedrops are of value in the treatment of various abnormal states of the eye such as dry eye syndrome. They can also serve as carrier for a variety of pharmaceutically active ingredients. Essential components are in combination water, an anionic polymer having a M.W. in the 500,000 to about 4,000,000 range at a concentration so that the viscosity measured at a 1 sec$^{-1}$ shear rate does not exceed about 150 cp. and a low molecular weight (of 500 or less M.W.) humectant polyol at a concentration of about isotonicity or slightly above. The solution must contain less than about 1.5 mM salt calculated as sodium chloride, not including the salts of the anionic polymeric viscosity enhancer, as higher concentrations destroy the non-Newtonian rheological properties. A process for treating dry eye syndrome by application of such eyedrops.

9 Claims, 4 Drawing Sheets

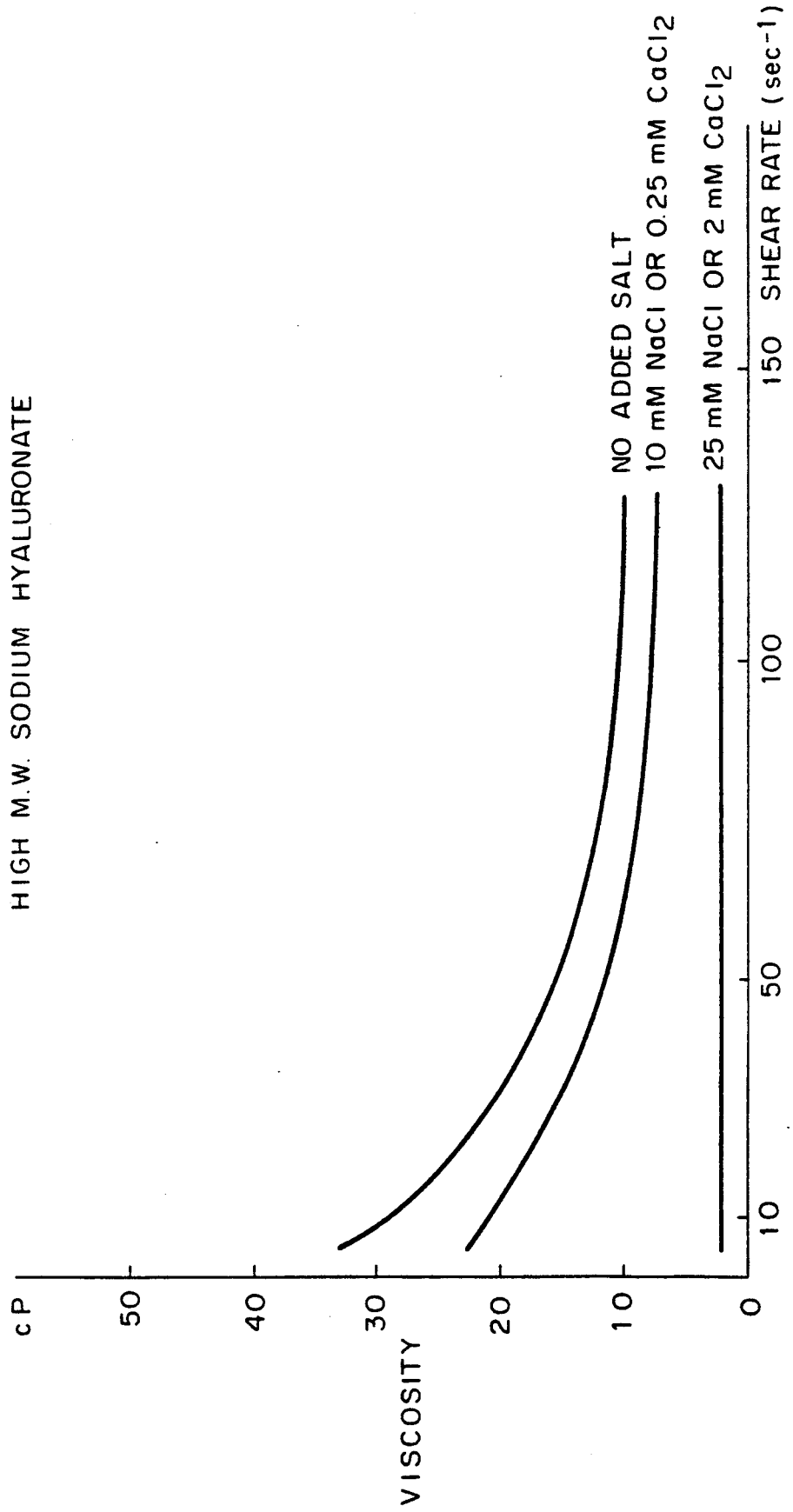

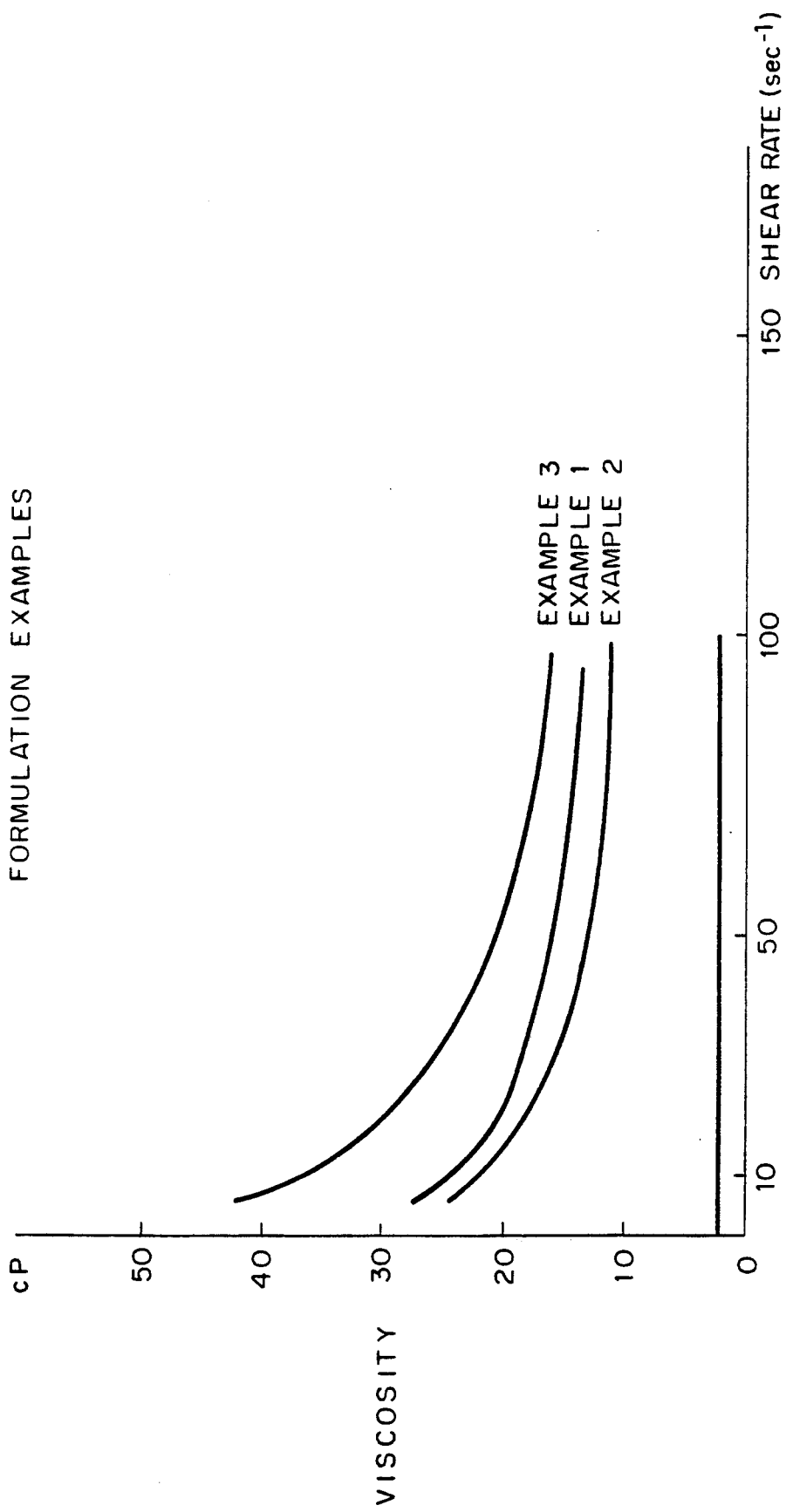

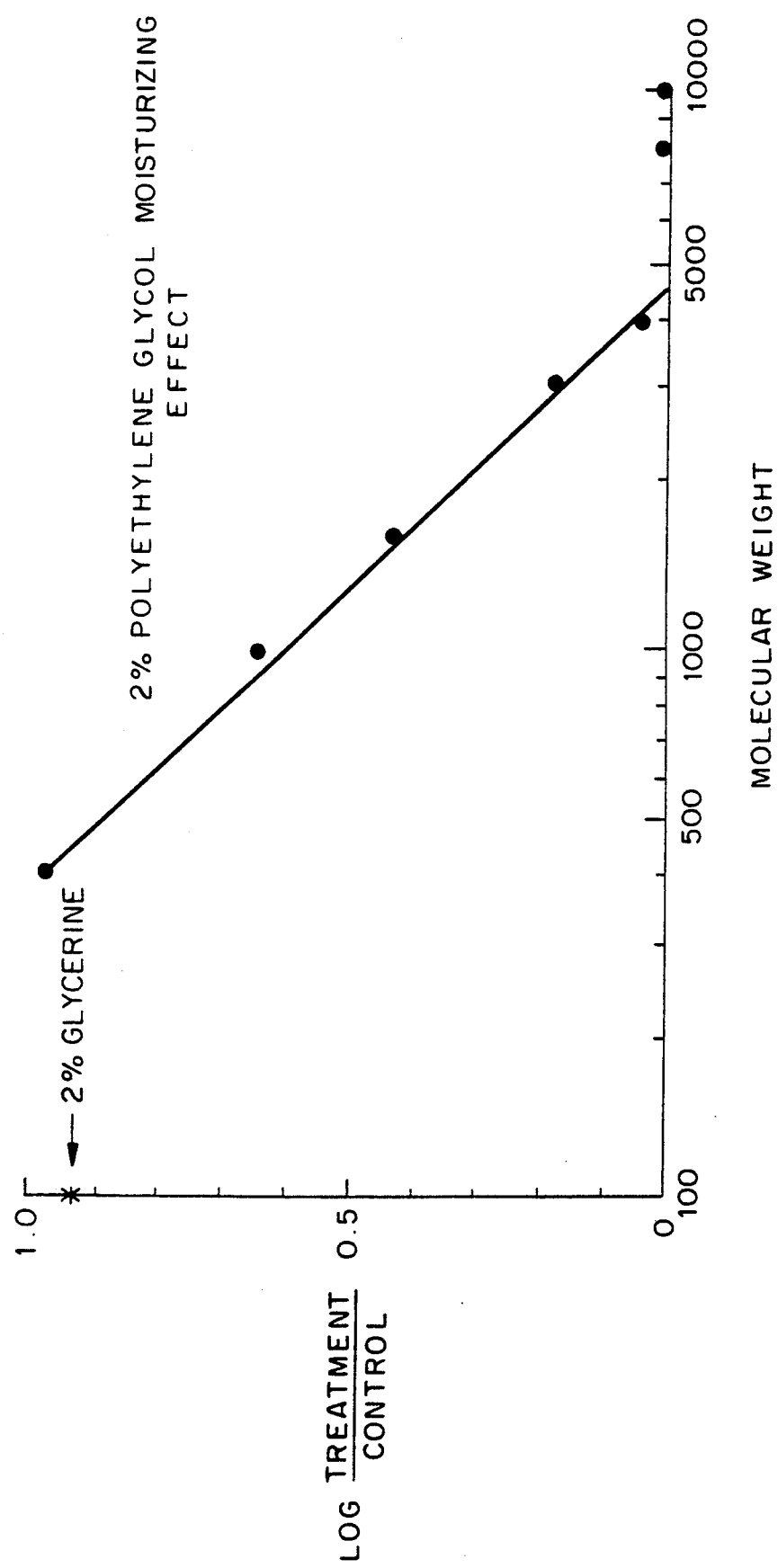

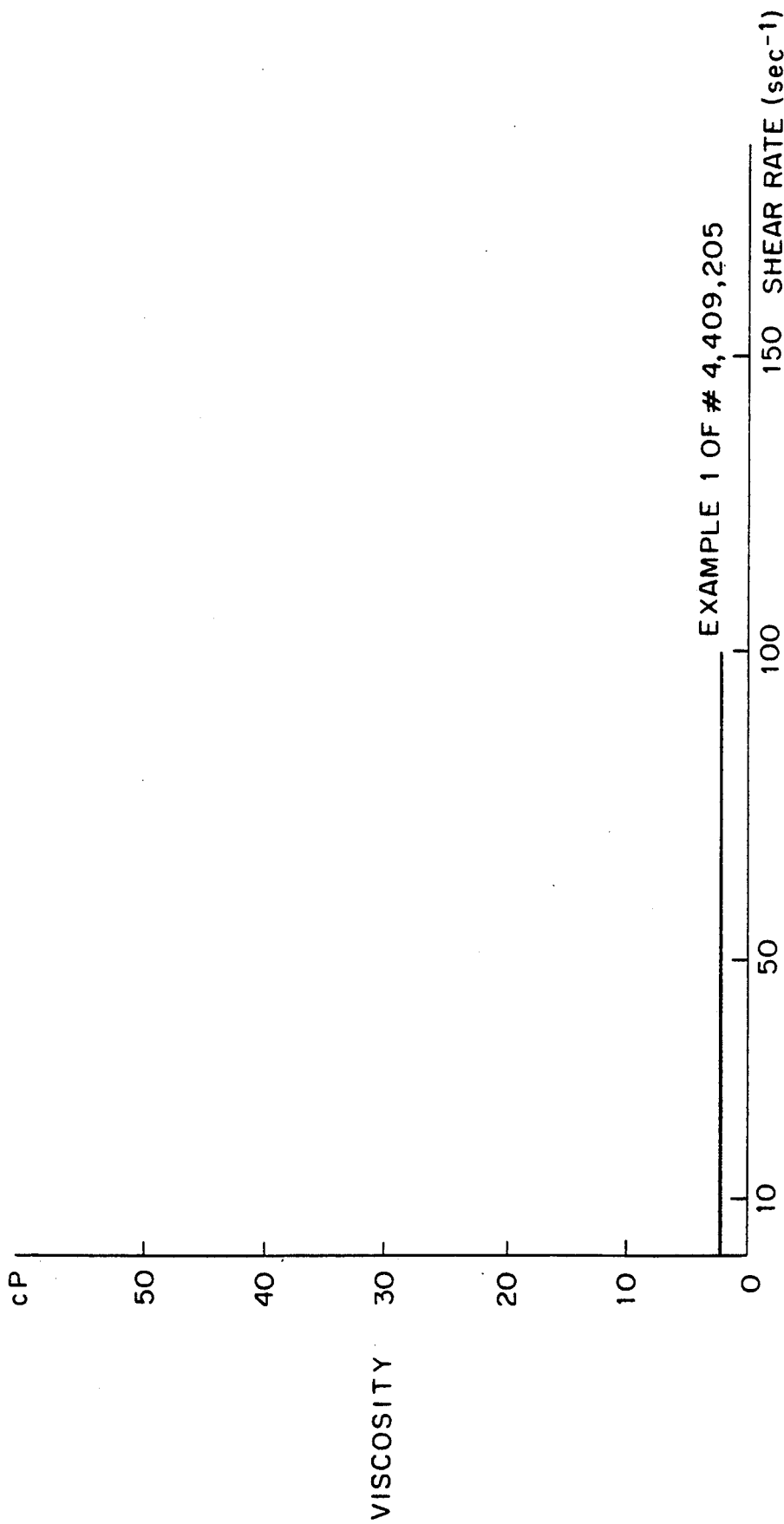

EYEDROPS HAVING NON-NEWTONIAN RHEOLOGICAL PROPERTIES

STATUS OF APPLICATION

The present application is a continuation-in-part application of abandoned U.S. patent application Ser. No. 07/350,286 filed May 11, 1989, which is a continuation-in-part application of abandoned U.S. patent application Ser. No. 07/107,575 filed Oct. 13, 1987.

FIELD OF INVENTION

The invention relates to isotonic humectant aqueous ophthalmic solutions which are of use in ophthalmology, and especially in cases of dry eye syndrome. They are also of value in the treatment of a variety of eye diseases and especially in infectious diseases etc.

The ophthalmic solutions contain in combination an effective humectant, generally in isotonic concentration, and an anionic polymer which is used to obtain a predetermined viscosity, the solutions being characterized by a non-Newtonian rheology. The viscosity decreases in a pronounced manner upon application of a mechanical force, as is the case during the blinking of a human eye: the decrease is at least by a factor of 2 times and preferably by a factor of 3 to 4. The viscosity of the natural tear film decreases in a pronounced manner upon application of mechanical shear, see A J Bron, Prospects for the dry Eye; Trans Ophthalmol. Soc 104 (1985) 801-826.

It has been surprisingly discovered that the presence of salt, such as sodium chloride, destroys the non-Newtonian rheology, and thus it is stipulated that the solutions of the invention ought not to contain more than about 0.01 weight per cent.

The non-Newtonian rheological behavior of human tears has been described in Hamano and Mitsunaga, Japan J. Ophthalmol. (1973) 17, 209-299 and in Dudinski et al., Curr. Ther. Res. February 1983, 33, 322-337.

The novel eyedrops are especially useful in cases of dry eye syndrome.

To the best of the knowledge of the inventor there have not been known before eyedrops which combine highly effective humectant properties and a non-Newtonian rheology resembling that of human tears, i.e. eyedrops of low viscosity which substantially decreases upon application of a mechanical force.

BACKGROUND OF THE INVENTION

Various eye diseases require treatment by the application of liquid preparations, administered to contact the eye. Eyedrops are also frequently required by wearers of contact lenses. Dry eye disease is a serious condition which requires the repeated application of eye drops per day. Conventional eye drops are based on isotonic solutions of various inorganic salts, with or without "non-ionic" substances (see U.S. Pat. No. 4,409,205), frequently with an added high-molecular weight substance which increases the viscosity of the drops.

Amongst frequently used polymeric substances there may be mentioned methyl cellulose, hydroxy ethyl cellulose, polyvinyl alcohol, polyvinylpyrrolidone, hyaluronic acid, and the like. The viscosity is generally 1 cp to 30 cp.

It is known that at a viscosity of about above 15 cp a discomfort is experienced by most persons, see Adler C. A. et al. The Effect of Viscosity of the Vehicle on the Penetration of Fluorescein into the Human Eye, Exp. Eye Res. 11, 34-42 (1971) and Patton T. F. et al., Occular Evaluation of Polyvinyl Vehicle in Rabbits, J Pharm Sci. 64, 1312-1316, 1975. In view of this most eyedrops have a viscosity in the 2 cp to 5 cp range, even when it is known that a higher viscosity will result in a prolonged action. Therefore, isotonic solutions containing inorganic salts have drawbacks as regards viscosity and physiological characteristics, as solutions containing salts above a certain level do not undergo changes of viscosity upon application of a shear force.

Shively describes in U.S. Pat. No. 4,409,205 Ophthalmic Solutions, which have a salt (sodium chloride) content of from 0.1 weight per cent to about 7.5 weight per cent, in combination with a non-ionic polymer. Extensive experiments have shown that non-ionic polymers do not give solutions having non-Newtonian rheological properties. Furthermore, the salt content which is much above the upper limit stipulated according to the present invention would destroy any such properties, if these would have been present. It is clear that Shively did not intend to prepare non-Newtonian solutions, and he did never obtain such solutions by chance as his ingredients preclude such rheological properties.

Gressel, in WO 94/04681, provides a liquid ophthalmic composition comprising a polyanionic polymer for use as a long-lasting artificial tear. His product, as exemplified and as claimed, relates to a viscous liquid preparation containing 0.05% to 0.5 by weight of a polyanionic polymer in combination with sodium chloride as preferred tonicity agent. He actually exemplifies gels as evident from the viscosity data of all examples. The high sodium chloride content of Gressel will destroy non-Newtonian properties of all the compositions of the present invention.

The preparations of the present invention overcome to a large extent the drawbacks of this kind, since they have a certain viscosity at a low shear rate, which shear rate corresponds to that of an open eye, while when the eye blinks the viscosity of the composition decreases in a pronounced manner to the comfortable range of about 2 cp to about 15 cp, which mimics the behavior of natural tears.

None of patents WO 84/04861—Alcon, U.S. Pat. No. 4,620,979—Schachan or U.S. Pat. No. 4,540,568—Trager describe eye drops which are humectants and the viscosity of which is markedly shear dependent.

SUMMARY OF THE INVENTION

There are provided humectant isotonic eyedrops for the treatment of, and for the alleviation of the symptoms of dry eye syndrome. The novel eyedrops have a low viscosity and can easily be applied. They have non-Newtonian rheological properties, and upon application of a mechanical force their viscosity changes at least by a factor of two-fold: such mechanical force reduces the viscosity by a factor of at least 2, and preferably by a factor of 3. The unique humectant and rheological properties of the novel eyedrops are the result of a combination of a number of essential constituents, which are a high molecular weight, of the order of about 500,000 to about 5,000,000 and preferably in the range of 1,000,000 to about 2,000,000, anionic polymer, in such a concentration that the solution has a viscosity not above 150 cp measured at a shear rate of 1 sec$^{-1}$, as efficient humectant a low molecular weight (less than about 500 M.W.) polyol having strong water holding properties, which is used at a concentration corresponding to isotonicity of the tears or varying from isotonicity by up to about 10 per cent; it being stipulated that the aqueous eyedrop solution contains less than about 1.5 milli-mole (mM) of salt calculated as sodium chloride, not including the salts of the anionic viscosity enhancing polymer.

A preferred humectant polyol is glycerol. There can also be used humectant low molecular weight polyols, such as polyalkylene glycols. When the mechanical shear force is applied, as is the case during the blinking of an eye, the viscosity decreases by a factor of at least twofold, and preferably by a factor from three to four. Examples of such decreases are illustrated in enclosed FIGS. 1 and 2.

As stated above the viscosity at a low shear rate ought not to exceed about 150 cp; the preferred range of viscosity is up to about 120 cp, and a still more preferred range is from about 10 to about 70 cp at a shear rate of 1 $sec^{-1}$. When such an ophthalmic solution is applied to the human eye, no discomfort is experienced. When eye-blinking takes place, the mechanical force thus applied to the solution rapidly decreases its viscosity in a pronounced manner, and this prevents any discomfort.

The isotonic solutions of the invention can be used as carriers for various pharmaceutically effective agents, such as antimicrobials, antiviral agents and the like.

Amongst preferred high molecular weight anionic polymers, used as viscosity enhancing agents, are high molecular weight polyacrylates. Some of these are marketed under the trade designation of Carbomer, the most preferred being Carbomer 941; produced from anionic monomers. There may also be used a suitable hyaluronic acid as viscosity enhancer, having preferably a molecular weight of 1,000,000 to 2,500,000.

According to the present invention there is generally used less than 0.1 weight-% of the anionic polymer. In the case of hyaluronic acid alone this may be as high as 0.3 per cent, and is preferably about 0.1%. With polyacrylic polymers the concentration is generally less than about 0.05, and this gives the desired viscosity, as defined above. The concentration is always adjusted according to the molecular weight and the required viscosity:

The invention is illustrated with reference to the enclosed Figures, in which:

FIG. 1 is a graph of salt content versus viscosity at various shear rates;

FIG. 2 is a graph illustrating the rheological properties of the formulations according to the Examples;

FIG. 3 illustrates the moisturizing effect of 2 per cent by weight polyethylene glycol versus the molecular weight of the polyethylene glycol, and the effect of glycerol;

FIG. 4 illustrates the rheological properties of the composition according to Example 1 of U.S. Pat. No. 4,409,205 (Newtonian behavior).

DETAILED DESCRIPTION

There are provided isotonic eye drops for the treatment of, and for the alleviation of the symptoms of dry eye syndrome. The novel eye drops have advantageous properties as compared with conventional eye drops. The novel eye drops are based on the use of a humectant such as glycerol, or other physiologically acceptable humectant polyols, such as polyethyleneglycol of M.W. not above 500, and anionic viscosity enhancer, and they are charactered by a change of viscosity upon application of a mechanical shear force. When at rest, the viscosity is constantly larger than when a shear force is applied. Thus, when eye-blinking takes place, the viscosity decreases and no discomfort is caused to the person who has applied such eyedrops. The change of viscosity upon application of a shear is brought out by the enclosed drawings.

Such isotonic solutions can be used as carrier for various types of medications used in ophthalmology. They can be used, amongst others, as carrier for various antimicrobial agents (antibiotics, antiviral agents and the like). The glycerol, as well as the other substances used according to the present invention are by themselves humectant, i.e. they are capable of holding water.

The ophthalmic preparations according to the invention ought to include conventional adjuvants and auxiliaries, so as to prevent their deterioration storage. These are well known in the art and not indicated in the specific examples. Furthermore, in order to have proper viscosity, a suitable polymer has to be used.

Preferably the viscosity of the eyedrops is adjusted so as not to exceed about 40 cp to 70 cp at rest. The measurements are made at a very slow rate. When the eye blinks, the viscosity must go down rapidly to a lower value, preferably not to exceed about 15 cp and even lower. The eyedrops of the invention have this property of a rapid decrease of viscosity upon application of mechanical shear. Such non-Newtonian behavior decreases if a salt content is present in excess of about 1.5 millimole per liter of salt. This does not include salts of the anionic type viscosity enhancing agents. The shear rate with an open eye is to be about 1 $sec^{-1}$; whereas upon blinking this changes dramatically to a value of above 1000 $sec^{-1}$. Especially advantageous results were obtained by the use of hyaluronic acid or polyacrylate, either by itself or in combination with other physiologically acceptable high molecular weight substances. The eye drops are based on physiologically acceptable humectant. Humectants of choice are glycerol and other acceptable humectant polyols. These are organic non-ionic substances and very good results were obtained by the use of these.

The humectant properties of the preparations of the present invention are easily demonstrated by applying isotonic solutions of the invention to the skin of the forearm and by measuring the electrical conductivity, or capacitance of the stratum corneum resulting within half an hour after such application. An increase of such conductivity or capacitance is indicative of a humectant effect.

The humectants are always used in the form of an essentially isotonic solution. The eye drops are sterilized and, if required, suitable agents are added to prevent bacterial or fungal deterioration.

There were tested solutions of this type for treating dry eye disease. There were also prepared ophthalmic preparations comprising antimicrobials and antiviral agents wherein the carrier was an isotonic solution defined above.

FIG. 1 demonstrates the effect of salts on the viscosity-shear rate relationship of sodium hyaluronate. One can see, that 25 mM (0.15%) sodium chloride (about 1/6 of isotonic) completely abolishes the shear rate dependency of the viscosity. Calcium (and presumably other divalent cations) is even more efficient to abolish such dependency: 2 mM (0.022%) $CaCl_2$ is sufficient.

Surprisingly, the addition of isotonic glycerine (2.7%) has little effect on the general shape of the sodium hyaluronate curve with no added salt.

The invention illustrated with reference to the following examples, which are of an illustrative nature only, and which are of a non-limitative nature.

EXAMPLE 1

Isotonic Ophthalmic Solution

A solution was prepared containing:

| | | |
|---|---|---|
| Glycerol | | 2.75 g |
| Sodium hyaluronate | | 0.10 g |
| Water | up to | 100 ml |

EXAMPLE 2

Isotonic Ophthalmic Solution

An isotonic solution was prepared containing:

| | | |
|---|---|---|
| Glycerol | | 2.75 g |
| Carbomer 941* | | 0.03 g |
| Water | up to | 100 ml |

*High M.W. Polyacrylate.

EXAMPLE 3

Isotonic Ophthalmic Solution

An isotonic solution was prepared containing:

| | | |
|---|---|---|
| Glycerol | | 2.50 g |
| Carbomer 941* | | 0.015 g |
| Sodium hyaluronate | | 0.015 g |
| Water | up to | 100 ml |

*High M.W. Polyacrylate.

The viscosity shear rate curves are shown in FIG. 2. It has to be remarked that the exact shape of the curves are very much dependent on the molecular weight of the polymers used and the pH of the solution and may change even from batch to batch.

EXAMPLE 4

Isotonic Ophthalmic Antiviral Solution:

To 100 ml of the solution of Example 1, 2 and 3, there was added:
0.1 g Idoxuridine.

EXAMPLE 5

Isotonic Antiglaucoma Preparation:

To 100 ml of the solution of Example 1, 2 and 3, there was added:
2 g pilocarpine as polyanion preparation.

EXAMPLE 6

Isotonic Ophthalmic Antibacterial Preparation:

To 100 ml of the solution of Example 1, 2 and 3, there was added:
0.5 g Chloramphenicol.

EXAMPLE 7

Anti-inflammatory Ophthalmin Solution:

To 100 ml of the solution of Example 1, 2 and 3, there was added:
0.05 g dexamethason sodium phosphate.

The addition of drugs decreased the dependency of the viscosity on shear rate, but sufficient dependency remained for comfortable eye drops.

In all the examples, the solution was adjusted to about isotonicity and to a pH of slightly above 7.

Suitable conventional stabilizers and preservatives can be added and marketed in steril units.

A group of 20 patients suffering from dry eye syndrome was treated with the ophthalmic solution of Example 1.

With conventional preparations they required more than four applications of eye drops per day.

Using the composition of Example 1, the average required decreased to three applications daily.

Another average was tested with the Example 3 composition. Only two daily applications were needed.

Eye drops containing an anti-inflammatory solution as set out in Example 7 were used for the treatment of inflammations of the eye. The drops were well tolerated and good results were obtained without any irritation of the eye.

Relief was very rapid.

The combination of a humectant and of a high molecular weight anionic polymer in a suitable aqueous vehicle, which contains only such a quantity of salt as not to interfere with the shear dependence of the eyedrops. Imitates to a large extent the behavior of a tear film.

To the best of the knowledge of applicant no such eyedrops are known from the prior art.

I claim:

1. An aqueous ophthalmic isotonic moisturizing solution having pronounced non-Newtonian rheological properties;
   (i) containing an anionic polymer having molecular weight from about 500,000 to about 4,000,000 at a concentration resulting in a viscosity of not above 150 cp at 1 sec$^{-1}$ shear rate,
   which decreases to less than 30 cp sec$^{-1}$ at 100 sec$^{-1}$ shear rate,
   (ii) a humectant moisturizing polyol of molecular weight less than about 500, having strong water-holding properties, at essentially isotonic or slightly above or below isotonic concentration,
   which solution contains less than 1.5 millimole of monovalent or bivalent salts, not including the salts of the anionic polymer.

2. An ophthalmic solution according to claim 1, where the humectant is glycerol.

3. An ophthalmic solution according to claim 1, where the anionic polymer is a carbomer at a concentration of 0.05% by weight or less.

4. An ophthalmic solution according to claim 1, where the anionic polymer is a polymer having carboxylic groups selected from hyaluronic acid, polyacrylic acids, carbomers and mixtures thereof.

5. An ophthalmic solution according to claim 1, where humectant is 300 to 500 M.W. polyethylene glycol or polypropylene glycol of 300 to 500 M.W.

6. An ophthalmic composition according to claim 3, where the anionic polymer is carbomer 941.

7. An ophthalmic composition according to claim 1, where the anionic polymer is hyaluronic acid, which comprises up to 0.35 by weight of the compositions.

8. An ophthalmic composition according to claim 1, containing in addition an efficient concentration of an antibacterial agent, antiviral agent, antiglaucoma agent or antiinflammatory agent.

9. A method for alleviating the symptoms of dry eye syndrome which comprises applying to the eye an ophthalmic solution as claimed in claim 1.

* * * * *